United States Patent [19]

Weeks

[11] Plant 4,710

[45] May 5, 1981

[54] ROSE PLANT

[76] Inventor: O. L. Weeks, 4759 Philadelphia St., Chino, Calif. 91710

[21] Appl. No.: 140,118

[22] Filed: Apr. 14, 1980

[51] Int. Cl.[3] ..... A01H 5/00

[52] U.S. Cl. ..... Plt./28

[58] Field of Search ..... Plt./27

*Primary Examiner*—Robert E. Bagwill

*Attorney, Agent, or Firm*—Vincent G. Gioia

[57] ABSTRACT

A new floribunda rose variety of vibrant red coloring, substantially non-fading and long lasting on the plant and as a cut flower.

1 Drawing Figure

The present invention relates to a new and distinct variety of rose plant of the floribunda rose class, which was originated by my crossing as seed parent the rose known as "Plain Talk" and the rose known as "Suspense" as pollen parent.

Among the novel characteristics possessed by this new variety which distinguish it from its parents and all other varieties of which I am aware are vibrant red colored, substantially non-fading flowers borne in medium clusters and a vigorous, free branching plant with abundant foliage. Flowers are dark red upon opening but petals show a yellow coloring on the reverse (under surface). Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusually fine floribunda rose with medium sized clusters of blooms displayed on a vigorous bushy, free branching plant with abundant foliage. The flowers are of heavy petalage but open well in all weather. The brilliant red coloring holds well upon aging.

The accompanying drawing shows typical specimens of the vegative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45C" is plate 45C of the Royal Horticultural Society Color Chart.

Parentage: Seedling.

*Seed parent.*—"Plain Talk".

*Pollen parent.*—"Suspense".

Class: Floribunda.

The following observations are made of specimens grown outdoors in San Bernardino County, Calif., during the month of October.

FLOWER

Blooming Habit: Continuous.

A. *Bud.*—(1) Size: Small. (2) Form: Ovoid to urn shaped with foliacious appendages extending beyond bud. (3) Color: After sepals open, predominant color of the underside of the first petals is 45C to 45D. Incompletely formed petals may also appear. As petals unfurl, though still in bud form, underside of petals is seen displaying yellow and red bicoloring. Underside of petals at point of attachment is 16C (buttercup yellow) lightening to 11D as color washes into the red petal edge 46A, and some light veining is also visible. (4) Sepals: Longer than bud, serrated tips, recurve downward. (5) Peduncle: Length—short, numerous small reddish green hairs. Aspect—straight. Strength—erect. Color—reddish grey green.

B. *Bloom.*—(1) Size: Average size when fully expanded—about 3 to 3½ inches. (2) Borne: Singly and in small clusters of 4 to 5 blooms. (3) Form: Cupped, becoming flat upon opening. (4) Petalage: Number of petals under normal conditions — about 46 to 50. (5) Color: As buds open and with fewer petals' undersurfaces visible, predominant flower color (petal top surface) is 44A. Color is relatively constant except for occasional white petal streak and visible lighter colored petaloids. Color is brilliant red with no noticeable bluing on aging.

C. *Petals.*—(1) Texture: Thick. (2) Appearance: Velvety to leathery. (3) Form: Rounded, wavy. (4) Arrangement: Regularly arranged. (5) Petaloids in center: Noticeable. (6) Persistence: Drop off cleanly. (7) Fragrance: Slight. (8) Lasting quality: Long lasting on plant and as cut flower.

REPRODUCTIVE ORGANS

A. Stamens, filaments and anthers:

(1) *Arrangement.*—Many stamens regularly arranged about pistils, short white filaments with yellow anthers.

B. Pollen: Color—yellow.

C. Styles: Uneven, thin, bunched.

D. Stigmas: Color—yellowish brown.

PLANT

A. Form: Upright, bushy.

B. Growth: Vigorous, free branching.

C. Foliage: Compound 3 to 7 leaflets.

(1) *Size.*—Small to medium.

(2) *Quantity.*—Abundant.

(3) *Color.*—New foliage: very young—reddish green. Upper side—near to 189A. Under side— near to 195A. Old foliage: Upper side—136A. Under side—139C.

(4) *Shape.*—Ovoid, mucronate.

(5) *Texture.*—Upper side is glossy and under side is dull or matte.

(6) *Edge.*—Serrated.

(7) *Serration.*—Simple.

(8) *Leaf Stem.*—Color—near to 139C. Under side—near to 139C.

(9) *Stipules.*—Long.

(10) *Resistance to disease.*—Blackspot—good. Rust—good.

D. Wood:

(1) *New wood.*—Color—green mixed with 59A. Bark—smooth, shiny.

(2) *Old wood.*—Color—near 138A. Bark—smooth, shiny.

E. Thorns:

(1) *Thorns.*—Quantity (main stalk): ordinary. Form—straight. Length—medium. Color—light brown. Position—scattered.

(2) *Prickles.*—Few.

F. Winter hardiness: Good winter hardiness.

I claim:

1. A new and distinct variety of rose plant of the floribunda class, substantially as shown and described, characterized particularly by vibrant red colored substantially non-fading flowers borne in medium sized clusters and showing yellow coloring on reverse of petals.

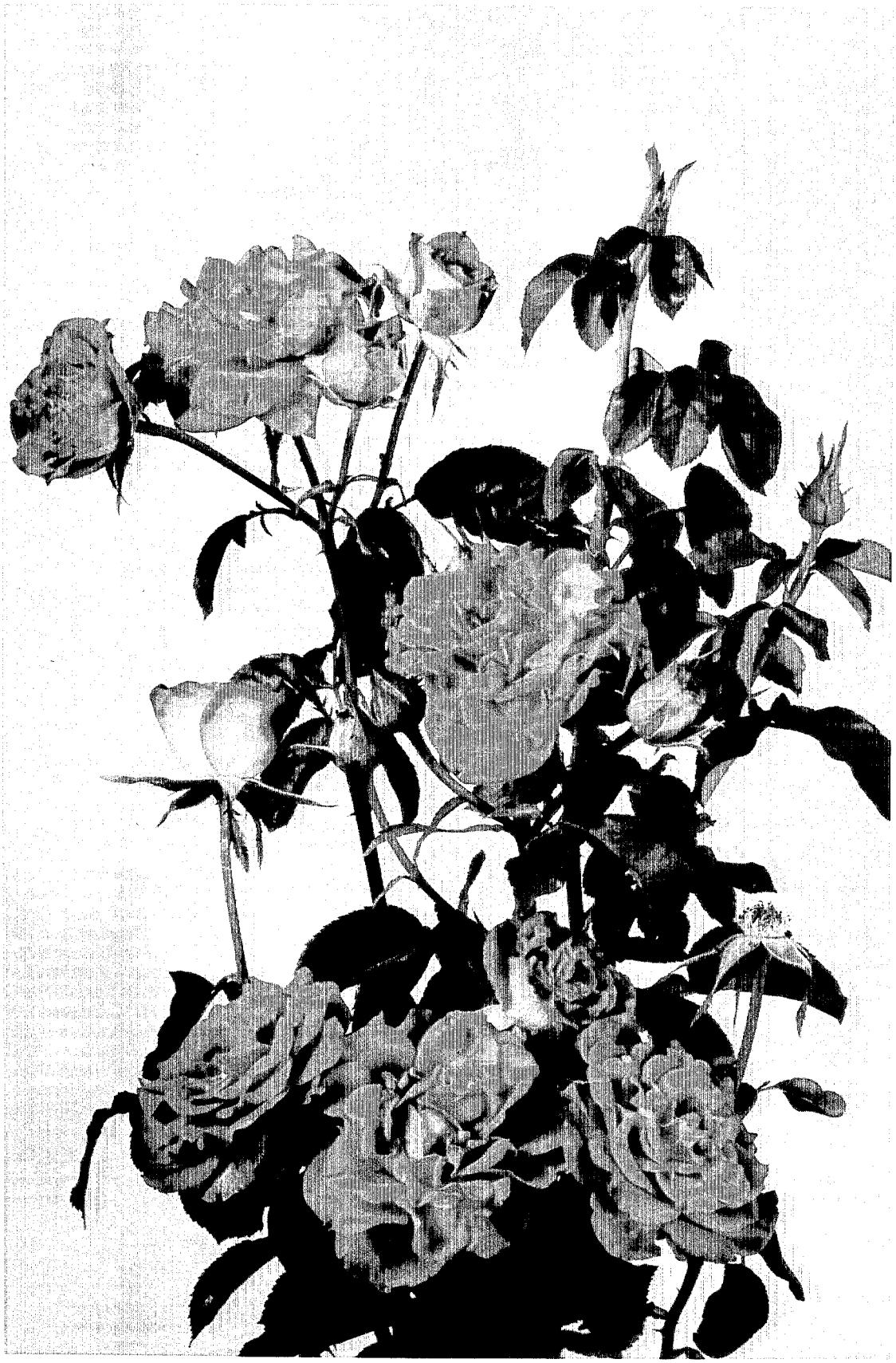

* * * * *